United States Patent
Schafer et al.

(10) Patent No.: US 10,261,212 B2
(45) Date of Patent: Apr. 16, 2019

(54) GENERATION OF DIFFRACTION SIGNATURE OF ITEM WITHIN OBJECT

(71) Applicant: ANALOGIC CORPORATION, Peabody, MA (US)

(72) Inventors: David Schafer, Rowley, MA (US); John P. O'Connor, Andover, MA (US)

(73) Assignee: Analogic Corporation, Peabody, MA (US)

( * ) Notice: Subject to any disclaimer, the term of this patent is extended or adjusted under 35 U.S.C. 154(b) by 345 days.

(21) Appl. No.: 14/907,325

(22) PCT Filed: Jul. 25, 2013

(86) PCT No.: PCT/US2013/052144
§ 371 (c)(1),
(2) Date: Jan. 25, 2016

(87) PCT Pub. No.: WO2015/012850
PCT Pub. Date: Jan. 29, 2015

(65) Prior Publication Data
US 2016/0170075 A1    Jun. 16, 2016

(51) Int. Cl.
*G01V 5/00*    (2006.01)
*G01N 23/04*    (2018.01)
(Continued)

(52) U.S. Cl.
CPC .......... *G01V 5/005* (2013.01); *G01N 23/046* (2013.01); *G01N 23/20* (2013.01); *G01N 23/20083* (2013.01); *G01V 5/0025* (2013.01)

(58) Field of Classification Search
CPC ................. G01N 23/046; G01N 23/20; G01N 23/20008; G01N 23/20083;
(Continued)

(56) References Cited

U.S. PATENT DOCUMENTS 5,007,072 A * 4/1991 Jenkins ................ G01N 23/201
378/57
5,265,144 A * 11/1993 Harding ................. A61B 6/032
378/147
(Continued)

FOREIGN PATENT DOCUMENTS

WO    2004/074871 A1    9/2004
WO    2004074871 A1    9/2004

OTHER PUBLICATIONS

First Chinese Office Action cited in Chinese Application No. 201380078724.1 dated Nov. 27, 2017, 12 pgs.
(Continued)

*Primary Examiner* — Allen C. Ho
(74) *Attorney, Agent, or Firm* — TraskBritt

(57) ABSTRACT

A diffraction system configured to generate a diffraction signature based upon an angular disbursement of radiation is provided. In some embodiments, the diffraction system comprises a radiation source comprising a radiographic isotope configured to natural emit radiation due to decay. In some embodiment, the diffraction system is part of an object identification system that comprises one or more other radiation imaging modalities, such as a CT system and/or a line-scan system. By way of example, the one or more other radiation imaging modalities may perform an initial examination of an object to generate data indicative of the object. The data can be analyzed to identify an item of interest within the object, which can subsequently be examined by the diffraction system to generate a diffraction signature of the item. The diffraction signature of the item can be compared to known diffraction signatures of know items to characterize the item.

18 Claims, 7 Drawing Sheets

(51) Int. Cl.
*G01N 23/20* (2018.01)
*G01N 23/046* (2018.01)

(58) Field of Classification Search
CPC ........... G01N 23/20091; G01N 23/201; G01V 5/0008; G01V 5/0016; G01V 5/0025; G01V 5/0041; G01V 5/005
USPC ...... 378/5, 9, 16, 19, 57, 70, 71, 87, 88, 90, 378/98.9
See application file for complete search history.

(56) References Cited

U.S. PATENT DOCUMENTS

| | | | |
|---|---|---|---|
| 5,600,303 A | 2/1997 | Husseiny et al. | |
| 5,638,420 A | 6/1997 | Armistead | |
| 5,696,806 A * | 12/1997 | Grodzins | G01N 23/046 378/86 |
| 6,054,712 A * | 4/2000 | Komardin | A61B 6/483 250/363.06 |
| 6,122,344 A * | 9/2000 | Beevor | G01V 5/0025 378/57 |
| 6,269,144 B1 * | 7/2001 | Dube | G01N 23/20 378/71 |
| 6,442,233 B1 * | 8/2002 | Grodzins | G01N 23/201 378/57 |
| 6,470,067 B1 * | 10/2002 | Harding | A61B 6/032 378/19 |
| 6,507,025 B1 * | 1/2003 | Verbinski | G01N 23/02 250/358.1 |
| 6,687,326 B1 * | 2/2004 | Bechwati | G01N 23/046 378/7 |
| 6,693,988 B2 * | 2/2004 | Harding | G01N 23/201 378/57 |
| 6,744,845 B2 * | 6/2004 | Harding | A61B 6/032 378/16 |
| 6,816,571 B2 * | 11/2004 | Bijjani | G01N 23/046 378/57 |
| 6,856,667 B2 * | 2/2005 | Ellengogen | G01V 5/0025 378/189 |
| 6,879,657 B2 * | 4/2005 | Hoffman | A61B 6/032 378/19 |
| 6,956,925 B1 * | 10/2005 | Hoffman | A61B 6/032 378/11 |
| 7,065,175 B2 * | 6/2006 | Green | G01N 23/20 378/57 |
| 7,092,485 B2 * | 8/2006 | Kravis | G01N 23/20 378/57 |
| 7,099,436 B2 * | 8/2006 | Francke | A61B 6/483 250/385.1 |
| 7,108,421 B2 * | 9/2006 | Gregerson | A61B 6/032 378/197 |
| 7,263,160 B2 * | 8/2007 | Schlomka | G01V 5/0016 378/57 |
| 7,283,613 B2 * | 10/2007 | Harding | G01V 5/0025 378/57 |
| 7,298,812 B2 * | 11/2007 | Tkaczyk | A61B 6/032 378/4 |
| 7,324,625 B2 * | 1/2008 | Eilbert | A61B 6/032 378/57 |
| 7,324,627 B2 * | 1/2008 | Harding | G01V 5/0025 378/62 |
| 7,327,853 B2 * | 2/2008 | Ying | G01T 1/2985 378/57 |
| 7,356,115 B2 * | 4/2008 | Ford | G01N 23/046 378/4 |
| 7,366,281 B2 * | 4/2008 | Skatter | G01V 5/0016 340/531 |
| 7,366,282 B2 * | 4/2008 | Peschmann | G01N 23/04 378/46 |
| 7,412,022 B2 * | 8/2008 | Jupiter | G01N 23/046 250/363.06 |
| 7,417,440 B2 * | 8/2008 | Peschmann | G01V 5/0016 250/250 |
| 7,418,073 B2 * | 8/2008 | Schlomka | A61B 6/032 378/6 |
| 7,453,974 B2 * | 11/2008 | Van Steven-Daal | A61B 6/032 378/207 |
| 7,463,720 B2 * | 12/2008 | Harding | G01V 5/0025 378/147 |
| 7,474,728 B2 * | 1/2009 | Schlomka | A61B 6/032 378/6 |
| 7,474,786 B2 * | 1/2009 | Naidu | G01V 5/0008 382/168 |
| 7,477,725 B2 * | 1/2009 | Harding | G01V 5/0016 378/146 |
| 7,486,760 B2 * | 2/2009 | Harding | G01N 23/20 378/7 |
| 7,499,523 B2 * | 3/2009 | Harding | G01N 23/20083 378/86 |
| 7,502,437 B2 * | 3/2009 | Schlomka | A61B 6/032 378/6 |
| 7,519,152 B2 * | 4/2009 | Smith | G01N 23/20 378/150 |
| 7,519,154 B2 * | 4/2009 | Harding | G01N 23/207 378/73 |
| 7,529,340 B2 * | 5/2009 | Harding | G01N 23/207 378/70 |
| 7,529,341 B2 * | 5/2009 | Schlomka | G01V 5/0025 378/57 |
| 7,539,337 B2 * | 5/2009 | Simanovsky | G01T 1/2985 382/131 |
| 7,551,709 B2 * | 6/2009 | Schlomka | A61B 6/032 378/57 |
| 7,564,947 B2 * | 7/2009 | Cernik | G01N 23/046 378/70 |
| 7,580,499 B2 * | 8/2009 | Van Stevendaal | G06T 11/006 378/19 |
| 7,583,783 B2 * | 9/2009 | Harding | G01N 23/046 378/4 |
| 7,587,021 B2 * | 9/2009 | Schlomka | A61B 6/032 378/6 |
| 7,587,026 B2 * | 9/2009 | Harding | G01N 23/201 378/70 |
| 7,590,215 B2 * | 9/2009 | Schlomka | A61B 6/032 378/4 |
| 7,623,616 B2 * | 11/2009 | Ziegler | A61B 6/032 378/5 |
| 7,646,850 B2 * | 1/2010 | MacDonald | G01N 23/20 378/86 |
| 7,668,289 B2 * | 2/2010 | Proksa | G01N 23/046 378/19 |
| 7,692,650 B2 * | 4/2010 | Ying | A61B 6/482 345/424 |
| 7,693,261 B2 * | 4/2010 | Robinson | G01N 23/04 378/57 |
| 7,697,664 B2 * | 4/2010 | Harding | G01N 23/207 378/71 |
| 7,702,073 B2 * | 4/2010 | Harding | G21K 1/025 378/149 |
| 7,720,194 B2 * | 5/2010 | Connelly | G01V 5/0016 378/57 |
| 7,742,563 B2 * | 6/2010 | Edic | G01N 23/20 378/57 |
| 7,756,249 B1 * | 7/2010 | Harding | H01J 35/02 378/87 |
| 7,773,724 B2 * | 8/2010 | Harding | G01V 5/0025 378/71 |
| 7,801,348 B2 * | 9/2010 | Ying | G01V 5/0041 382/131 |
| 7,835,495 B2 * | 11/2010 | Harding | G01N 23/20083 378/87 |
| 7,844,027 B2 * | 11/2010 | Harding | G01V 5/00 378/20 |
| 7,856,081 B2 * | 12/2010 | Peschmann | G01N 23/223 378/46 |
| 7,869,566 B2 * | 1/2011 | Edic | G01V 5/005 378/57 |

(56) References Cited

U.S. PATENT DOCUMENTS

| | | | | |
|---|---|---|---|---|
| 7,874,730 | B2* | 1/2011 | Harding | G01N 23/20083 378/207 |
| 7,876,879 | B2* | 1/2011 | Morton | G01T 1/2985 378/57 |
| 7,881,437 | B2* | 2/2011 | Harding | G21K 1/025 378/149 |
| 7,894,568 | B2* | 2/2011 | Ziegler | G01T 1/2985 378/5 |
| 7,961,839 | B2* | 6/2011 | Ziegler | G06T 11/005 378/19 |
| 8,005,189 | B2* | 8/2011 | Ripp | G01V 5/0008 190/102 |
| 8,009,883 | B2* | 8/2011 | Ying | G01V 5/0008 382/128 |
| 8,033,725 | B2* | 10/2011 | Maack | A61B 6/583 378/207 |
| 8,047,053 | B2* | 11/2011 | Call | G01N 1/2202 73/28.01 |
| 8,090,150 | B2* | 1/2012 | Garms | G01V 5/0016 378/57 |
| 8,135,197 | B2* | 3/2012 | Forthmann | G06T 11/008 378/4 |
| 8,139,717 | B2* | 3/2012 | Harding | G21K 1/025 378/147 |
| 8,180,138 | B2* | 5/2012 | Basu | G01V 5/0008 382/141 |
| 8,180,139 | B2* | 5/2012 | Basu | G01V 5/0041 382/141 |
| 8,223,919 | B2* | 7/2012 | Morton | G01N 23/046 378/57 |
| 8,451,974 | B2* | 5/2013 | Morton | G21K 1/025 378/57 |
| 8,693,621 | B2* | 4/2014 | Thran | A61B 6/4021 378/17 |
| 9,086,366 | B2* | 7/2015 | Schmitt | G01N 23/20 |
| 9,110,004 | B2* | 8/2015 | Feser | G01N 23/046 |
| 9,113,839 | B2* | 8/2015 | Morton | A61B 6/032 |
| 9,299,001 | B2* | 3/2016 | Litvin | G01V 5/0008 |
| 9,335,281 | B2* | 5/2016 | Marks | G01N 23/201 |
| 9,355,502 | B2* | 5/2016 | Litvin | G01N 23/046 |
| 9,572,540 | B2* | 2/2017 | Zhang | H01L 27/14634 |
| 9,696,452 | B2* | 7/2017 | Schafer | A61B 6/032 |
| 9,846,935 | B2* | 12/2017 | Simanovsky | G01V 5/0008 |
| 2004/0109532 | A1 | 6/2004 | Ford et al. | |
| 2006/0140340 | A1 | 6/2006 | Kravis | |

OTHER PUBLICATIONS

Preliminary Report cited in PCT Application No. PCT/US2013/052144 dated Jan. 26, 2014, 7 pgs.

International Search Report cited in related application No. PCT/US12/052144 dated Mar. 27, 2014, pp. 11.

Harding, et al., "Radiation source considerations relevant to Next-Generation X-ray Diffraction Imaging for security screening applications", Aug. 2, 2009, pp. 1-11.

Chen, et al., "X-ray Diffraction Tomographic Imaging and Reconstruction", http://www.northeastern.edu/alert/assets/F3_p4_Castanon_Chen.pdf, Jul. 21, 2011, p. 1.

Harding, et al., "Coherent X-ray scatter imaging and its applications in biomedical science and industry", 1999, pp. 229-245.

Written Opinion of the International Searching Authority for PCT Application No. PCT/US2013/052144 dated Mar. 27, 2014, six pages.

* cited by examiner

GENERATION OF DIFFRACTION SIGNATURE OF ITEM WITHIN OBJECT

CROSS-REFERENCE TO RELATED APPLICATIONS

This application is a national phase entry under 35 U.S.C. § 371 of International Patent Application PCT/US2013/052144, filed Jul. 25, 2013, designating the United States of America and published in English as International Patent Publication WO 2015/012850 A1 on Jan. 29, 2015.

BACKGROUND

The present application relates to the field of object recognition, and in particular to object recognition techniques that utilize ionizing radiation to determine one or more physical characteristics and/or morphological characteristics of an object under examination. It finds particular application in the context of security imaging where it may be desirable to identify potential threat items concealed within an object (e.g., a suitcase, purse, human, etc.). However, it may also find applicability in medical fields, industrial fields, and/or other fields where radiation imaging modalities are employed to examine and/or image an object.

Today, radiation imaging modalities such as computed tomography (CT) systems, single-photon emission computed tomography (SPECT) systems, projection systems, and/or line-scan systems, for example, are useful to provide information, or images, of interior aspects of an object under examination. Generally, the object is exposed to radiation comprising photons (e.g., x-rays, gamma rays, etc.), and an image(s) is formed based upon the radiation absorbed and/or attenuated by interior aspects of the object, or rather an amount of radiation photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation imaging modalities are utilized in a variety of fields to examine and/or image aspects of an object not readily visible to the naked eye. For example, radiation imaging modalities are used in security applications to identify potential threat items, such as weapons and/or explosives that may be concealed within a suitcase, bag, or person, for example. Two of the more commonly used radiation imaging modalities in security applications are CT systems and line-scan systems. Line-scan systems are configured to view the object from a limited number of angles and generate projection images (e.g., two dimensional images) respectively representing a collapsed or flattened, two-dimensional view of the object (e.g., where the densities of various items along a line in which radiation travels are integrated and represented as a single point on the image). CT systems are configured to view an object from a plurality of angles (e.g., at least 180 degrees but often 360 degrees) to generate volumetric data representative of the object. In this way, a 3D image of the object can be created and properties of respective items within the object, such as density information, Z-effective information, shape characteristics, etc. can be determined based upon data indicative of the 3D image.

In some embodiments, data generated from an examination of an object is analyzed by the radiation imaging modality using automatic threat analysis algorithms to determine if the object comprises a potential threat item and/or other item of interest. For example, the radiation imaging modality may analyze a projection image generated by a line-scan system to determine if an outline of a weapon can be identified and/or may analyze data related to a three-dimensional image generated by a CT system to determine if an organic explosive is potentially comprised within the object.

While automatic threat analysis algorithms have proven useful to identify potential threat items and/or other items of interest, such algorithms may, at times, mischaracterize an item, resulting in a false positive. In a security application this may result in non-threat items being incorrectly classified as a potential threat item. Accordingly, objects flagged as comprising a potential threat item and/or other item of interest may have to be resolved by some other method(s), such as a visual inspection of image(s), hand search of the items, and/or via use of some other screening technology.

BRIEF SUMMARY

Aspects of the present application address the above matters, and others. According to one aspect, a system for generating a diffraction signature of an item within an object is provided. The system comprises a radiation source comprising a radiographic isotope configured to expose the item to radiation and a detector array configured to detect radiation that interacts with the item. The system also comprises a diffraction signature component configured to generate the diffraction signature of the item based upon an angular disbursement of the radiation that interacts with the item.

According to another aspect, a method for determining a molecular composition of an item within an object is provided. The method comprises performing a first examination on an object via first radiation to generate data indicative of the object and analyzing the data to identify the item within the object. The method also comprises performing a second examination on the item via second radiation generated from decay of a radiographic isotope and generating a diffraction signature of the item based upon an angular disbursement of the second radiation upon interaction with the item. The method further comprises using the diffraction signature to determine a molecular composition of the item.

According to yet another aspect, an object identification system is provided. The system comprises a radiation imaging modality configured to examine an object via first radiation. The radiation imaging modality comprises a first radiation source configured to emit radiation photons having a range of energy levels, a first detector array configured to detect radiation photons that interact with the object and to generate data indicative of the object based upon the detected radiation photons, and a threat detection component configured to identify an item within the object for examination by a diffraction system based upon the data indicative of the object. The system also comprises the diffraction system configured to generate a diffraction signature of the item. The diffraction system comprises a second radiation source configured to emit monoenergetic radiation toward the item, a second detector array configured to detect second radiation that interacts with the item, and a diffraction signature component configured to generate the diffraction signature of the item based upon an angular disbursement of the second radiation that interacts with the item.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
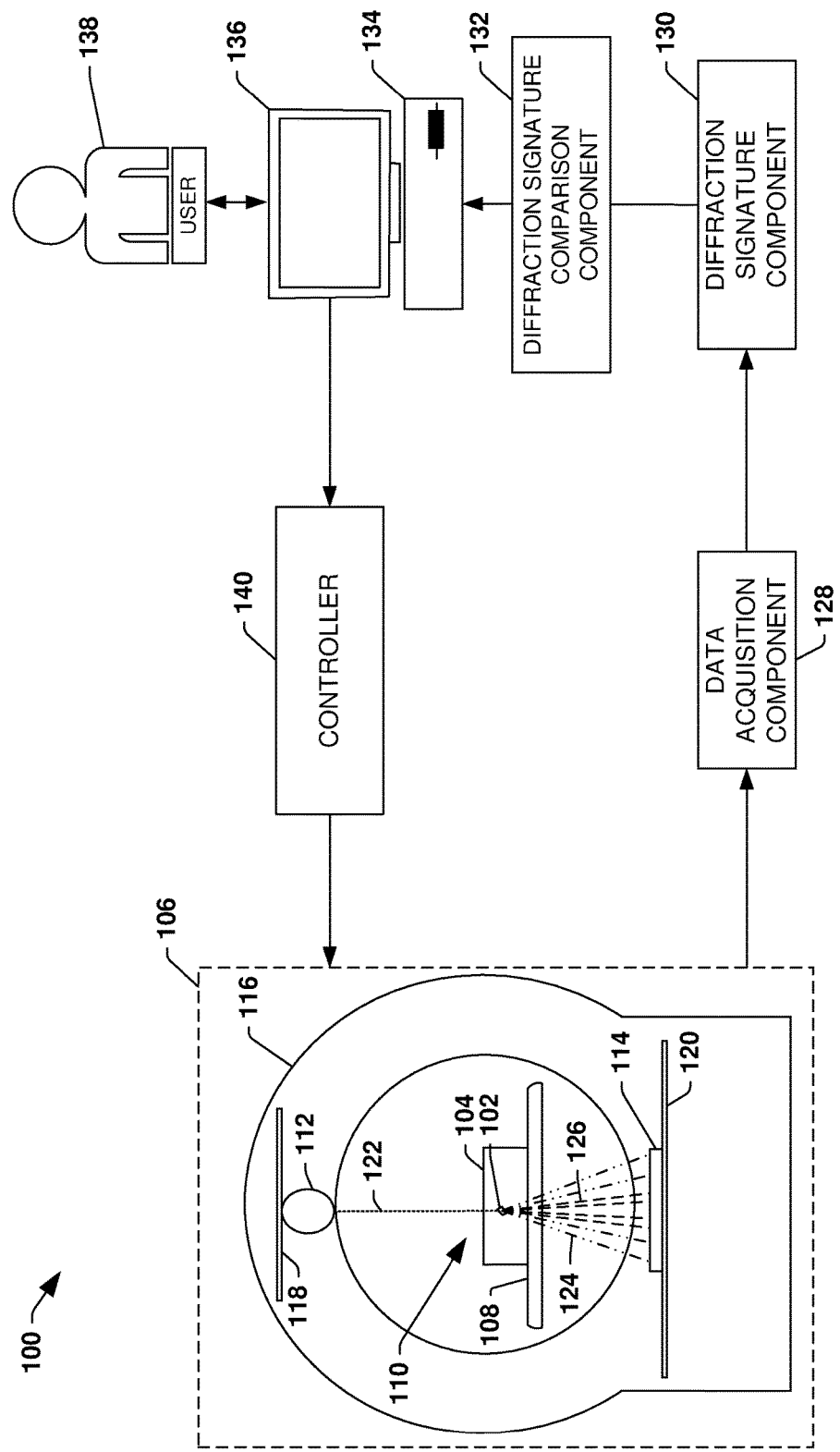
FIG. 1 is a schematic block diagram illustrating an example diffraction system.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are described herein for a diffraction system configured to examine an item within an object to determine a molecular composition of the item. In some embodiments, the diffraction system may be a secondary examination system configured to reexamine at least a portion of the object (e.g., to reduce false positives as a security checkpoint). By way of example, the diffraction system may be coupled to a computed tomography (CT) system, line-scan system, or other radiation imaging modality configured to examine an object. Data generated by the CT system and/or the line-scan system may be analyzed to identify whether the object comprises an item of interest (e.g., a potential threat item). In instances where such an analysis is associated with a low confidence (e.g., where there is a specified degree of uncertainty regarding whether the item is an item of interest) and/or in instances where an item of interest is positively identified, the object may undergo additional screening via the diffraction system to determine the molecular composition of the item (e.g., which may be used to verify that the item is an item of interest). In some embodiments, the diffraction system is merely configured to examine an item(s) within the object that is associated with the low confidence and/or an item(s) that is positively identified as an item of interest. Accordingly, in such embodiments, the diffraction system merely examines a portion of the object and is not tasked with examining the entire object.

The diffraction system comprises a radiation source configured to emit (e.g., pencil-like) beams of radiation and a detector array configured to detect radiation that interacts with the item to determine an angular disbursement of the radiation. In some embodiments, the radiation source comprises a radiographic isotope (e.g., cesium-137, cobalt-57, etc.) configured to naturally generate radiation. In other embodiments, the radiation source is coupled to a high power voltage source and is configured to generate radiation when a sufficient voltage bias is applied between an anode and a cathode of the radiation source.

When radiation emitted by the radiation source interacts with an item to which the radiation beams are targeted, radiation photons may be absorbed by the item, scattered by the item, or may pass linearly through the item. Radiation photons that are scattered by the item may be divided into incoherent scatter and coherent scatter. Incoherent scatter refers to radiation photons that lose energy upon being deflected by the item (e.g., at least some of the energy is transferred from the photon to the item). Coherent scatter refers to radiation photons that do not lose energy upon being deflected by the item (e.g., the radiation photon has the same, or at least substantially the same, energy before and after the deflection).

The disbursement of coherent scatter may be indicative of a molecular composition of the item exposed to the radiation beams. That is, stated differently, a first item having a first molecular composition may cause coherent scatter to be disbursed differently than a second item having a second molecular composition. Accordingly, the molecular composition of the item exposed to the radiation beam may be determined by detecting the angular disbursement of coherent scatter. In this way, the molecular composition of an item can be determined to assess whether the item is a potential threat item (e.g., such as an organic or inorganic explosive, a knife, etc.) and/or other item of interest.

To separate the coherent scatter from the incoherent scatter, numerous techniques are contemplated. For example, it has been observed for radiation generated by some radiographic isotopes that the deflection experienced by coherent scatter is less than the deflection experienced by incoherent scatter. For example, a statistically significant portion of the coherent scatter of 160 keV radiation may be typically deflected by less than 5 degrees relative to a linear path of the radiation beam from the radiation source to the detector array, whereas a statistically insignificant portion of the incoherent scatter of 160 keV radiation may be typically deflected by less than 5 degrees relative to the linear path. Accordingly, for purposes of the instant application, in some embodiments, it may be assumed that radiation detected within a specified cone of the linear path of the radiation beam (e.g., within a 5 degree cone of the linear path) is coherent radiation. In other embodiments, the energy of radiation photons impinging upon the detector array may be measured to separate coherent scatter from incoherent scatter (e.g., where coherent scatter refers to radiation photons that do not lose energy upon being deflected by the object and thus the energy of coherent scatter will be the same, or at least substantially the same, as the energy of the emitted radiation beam(s)).

FIG. 1 illustrates an example diffraction system 100 configured to examine an item 102 within an object 104 to determine the molecule composition of the item 102 and/or to determine whether the item 102 is a member of a class of items of interest (e.g., by comparing a diffraction signature of the item 102 to the diffraction signatures of known items). For example, in some embodiments, the diffraction system 100 may be configured to make a determination regarding whether the item 102 is a member of a class of items that are known to be potential threat items (e.g., organic explosives, inorganic explosives, guns, knives, etc.).

The diffraction system 100 comprises an examination unit 106 configured to examine an item 102 within an object 104. The object 104 is supported by a support article 108 (e.g., a bed, conveyor belt, etc.) configured to position the object 104 within an examination region 110 of the examination unit 106.

The examination unit 106 comprises a radiation source 112 (e.g., an ionizing radiation source such as an x-ray source or a gamma-ray source) and a detector array 114, which is positioned substantially diametrically opposite the radiation source 112 relative to the object 104. In the illustrated embodiment, a housing 116 shrouds the radiation source 112 and the detector array 114. Such a housing 116 may be configured to shield an environment outside of the examination unit 106 from radiation and/or to inhibit particulates from collecting on the radiation source 112 and/or the detector array 114, for example.

In some embodiments, the radiation source 112 and/or the detector array 114 are mounted to positioning apparatuses 118, 120 configured to position the radiation source 112 and/or the detector array 114 at a desired position(s) relative to the object 104 (e.g., to align a radiation beam 122 emitted from the radiation source 112 with the item 102). By way of example, the positioning apparatus 118 may comprise mechanically-actuated tracks and/or a robotic arm configured to move the radiation source 112 left and right on the page and/or into and out of the page to align the radiation beam 122 with the item 102. As another example, the positioning apparatus 120 may comprise mechanically-actuated tracks and/or a robotic arm configured to move the detector array 114 left and right on the page and/or into and out of the page to align a center of the detector array 114 with a center of the radiation beam 122. In some embodiments, the positioning apparatuses 118, 120 may be configured to rotate the radiation source 112 and/or detector array 114 clockwise and/or counterclockwise on the page (e.g., to align the radiation source 112 and/or the detector array 114 with a left or right side of the object 104).

During an examination of the item 102, the radiation source 112 emits a set of one or more radiation beams 122 (e.g., pencil beams of radiation) from a focal spot of the radiation source 112 (e.g., a region of the radiation source 112 from which radiation beams 122 emanate) toward the item 102. The radiation beam(s) 122 that is emitted from the radiation source 112 may be monoenergetic (e.g., radiation photons of the radiation beam 122 have a same energy) or non-monoenergetic (e.g., some radiation photons of the radiation beam 122 may have a first energy and other radiation photons of the radiation beam 122 may have a second energy).

In some embodiments, the radiation source 112 comprises a radiographic isotope, such as cesium-137, cobalt-57, and/or another isotope having an energy output and/or half-life suitable for an environment in which the diffraction system 100 is to be operated. By way of example, where the diffraction system 100 is utilized for cargo inspection, it may be desirable to select a radiographic isotope having an energy output of about 600 keV or more (e.g., due to the volume of cargo containers). As another example, a radiographic isotope having an energy output of about 60 keV may be selected for a diffraction system configured to examine carry-on luggage at an airport. Moreover, in some embodiments (e.g., as described with regard to FIG. 2) it may be desirable for the radiation source 112 to comprise two or more radiographic isotopes (e.g., a first radiographic isotope emitting radiation at a first energy and a second radiographic isotope emitting radiation at a second energy), and/or the examination unit 106 may comprise two or more radiation sources, a first radiation source comprising a first radiographic isotope and a second radiation source comprising a second radiographic isotope.

Radiographic isotopes release radiation naturally due to decay of the radiographic isotope. Accordingly, the radiation source 112 may comprise a shutter and/or collimator that is positioned over the focal spot to control the release of radiation beam(s) 122 from the radiation source 112 and/or to aim the radiation beam(s) 122 at the item 102. For example, at times when it is desirable to mitigate the leakage of radiation beam(s) 122 from the radiation source 112, the shutter may be closed. At other times when it is desirable to expose the item 102 to the radiation beam(s) 122, the shutter may be opened to release radiation beams 122 from the radiation source 112.

In other embodiments, the radiation source 112 is coupled to a high voltage power source and is configured to emit radiation beams 122 when a sufficient voltage bias is created between an anode and a cathode of the radiation source 112. That is, stated differently, the radiation source 112 is configured to generate radiation when an accelerating voltage (e.g., typically a voltage of about 30 kV to 180 kV or more depending upon a desired energy level or energy spectrum of the emitted radiation) is applied to the radiation source 112, causing electrons flowing out the cathode to be accelerated and impinge the anode at a high rate of speed.

Radiation photons of the radiation beam 122 may interact with the item 102 in one of several ways. For example, a radiation photon may be absorbed by the item 102 (e.g., where the energy associated with the radiation photon is completely absorbed by the item 102), may be scattered by the item 102 (e.g., where the radiation photon is deflected by the item 102), or may be unimpeded by the item 102 (e.g., allowing the radiation photon to continue traveling along a linear path between the radiation source 112 and the detector array 114). Radiation photons that are scattered by the item 102 may be categorized as incoherent scatter or coherent scatter. Incoherent scatter refers to radiation photons that lose energy upon interaction with the item 102 (e.g., a portion of the energy associated with the radiation photon is transferred from the radiation photon to the item 102), and coherent scatter refers to radiation photons that do not lose energy upon interaction with the item 102 (e.g., energy associated with the radiation photon is the same, or at least substantially the same, before and after the interaction with the item 102). In the illustrated embodiment, the trajectory of incoherent scatter is represented by the dash-dot-dot lines 124 and the trajectory of coherent scatter is represented by the dashed lines 126. It may be appreciated that while the example embodiment merely illustrates photons being scattered in a forward-direction of the detector array 114, radiation photons may be scattered in a multitude of directions and thus at least some of the incoherent scatter and/or coherent scatter may not impinge the detector array 114.

The detector array 114 is configured to detect radiation photons that have interacted with the item 102 and impinged a detection surface of the detector array 114. Such radiation photons may include radiation photons that were unimpeded by the item 102, incoherent scatter, and/or coherent scatter, for example. As will be further described with respect to FIG. 3, in some embodiments, the detector array 114 is further configured to inhibit radiation photons that were unimpeded by the item 102 from being detected. For example, a mask (e.g., 306 in FIG. 3) may be placed over a portion of the detector array 114 that would detect radiation photons that were unimpeded by the item 102.

The detector array 114 comprises a plurality of detector cells configured to directly convert and/or indirectly convert detected radiation photons into electrical charge to generate analog signals. Such analog signals may carry information indicative of the number of radiation photons detected by respective detector cells, an amount of electrical charge that has accumulated at respective detector cells over a sampling period, and/or an energy level of respective radiation photons detected by the detector array 114.

The detector array 114 may be an angular disbursement detector array or an energy disbursement detector array. An angular disbursement detector array refers to a detector array configured to resolve the location of radiation events on the detector array. That is, stated differently, an angular disbursement detector array refers to a detector array configured to output an analog signal indicative of where a radiation photon was detected and/or a number of radiation photons detected at a given location during a specified period of time. An energy disbursement detector array refers to a detector array configured to resolve the location and energy of radiation events on the detector array. That is, stated differently, an energy disbursement detector array refers to a detector array configured to output an analog signal indicative of where a radiation photon was detected and an energy of the radiation photon. In this way, where the radiation beam(s) 122 emitted from the radiation source 112 is monoenergetic, incoherent scatter can be distinguished from coherent scatter because the coherent scatter will have a substantially same energy as the radiation beam 122 emitted from the radiation source 112 whereas the incoherent scatter will have a different energy than the radiation beam(s) 122 emitted from the radiation source 112.

Analog signals generated by the detector array 114 or detector cells thereof may be transmitted to a data acquisition component 128 configured to convert the analog signals into digital signals and/or to compile signals that were transmitted within a predetermined time interval, or measurement interval, using various techniques (e.g., integration, photon counting, etc.).

The data acquisition component 128 may be operably coupled to a diffraction signature component 130 configured to generate a diffraction signature of the item 102 based upon an angular disbursement of at least some of the radiation photons that interacted with the item 102. The diffraction signature describes how at least some radiation photons were distributed across the detector array 114 during a measurement interval. For example, as further described with respect to FIG. 4, the diffraction signature component 130 may be configured to plot the number of radiation photons detected by respective detector cells on a two-dimensional line graph (e.g., where the y-axis may represent the number of radiation photons detected and the x-axis may represent detector cell). In other embodiments, other techniques for plotting the distribution of at least some of the detected photons are contemplated.

In some embodiments, the diffraction signature component 130 may be configured to generate the diffraction signature of the item 102 based upon the angular disbursement of a subset of the radiation photons that are detected by the detector array 114. By way of example, the diffraction signature component 130 may generate the diffraction signature based merely upon the angular disbursement of coherent scatter. Accordingly, in some embodiments, the diffraction signature component 130 may filter data representative of coherent scatter from data representative of incoherent scatter and/or from data representative of radiation photons that were unimpeded by the item 102 (e.g., followed a linear path from the radiation source 112 to the detector array 114).

Various techniques may be used to filter the data representative of coherent scatter from the data representative of incoherent scatter. For example, it has been observed that coherent scatter is typically more forward-directional than incoherent scatter. That is, the coherent scatter is deflected less by items of an object than incoherent scatter (e.g., the coherent scatter may be deflected by less than 5 degrees whereas incoherent scatter may be deflected by, on average, 10 degrees or more). Accordingly, the diffraction signature component 130 may assume that data corresponding to detector cells within a 5 degree cone, for example, relative to a linear path of the radiation beam(s) 122 from the radiation source 112 to the detector array 114 is indicative of coherent scatter and data corresponding to detector cells outside of the 5 degree cone is indicative of incoherent scatter. It may be appreciated that the angle of the cone may be a function of an energy of the emitted radiation beam(s) 122 (e.g., because incoherent scatter may become more forward-directional as the energy of the emitted radiation beam(s) 122 increases), and thus the cone angle may be greater or less than 5 degrees.

In other embodiments, the diffraction signature component 130 may be configured to filter the data representative of coherent scatter from the data representative of incoherent scatter based upon an energy of detected radiation photons. By way of example, data representative of radiation photons that have an energy that is less than the energy of the radiation beam(s) 122 emitted by the radiation source 112 may be identified as corresponding to incoherent scatter and may be filtered from data representative of radiation photons that have an energy that is substantially the same as the energy of the radiation beam(s) 122 emitted by the radiation source 112. In some embodiments, the filtering of data representative of coherent scatter from data representative of incoherent scatter based upon energy assumes that the radiation source 112 emitted a set of monoenergetic radiation beams 122 (e.g., where the radiation photons initially had a substantially same energy prior to interaction with the object 104 and/or item 102).

The diffraction signature of an item is indicative of a molecular composition of the item. By way of example, a first item having a first molecular composition would generate a first diffraction signature and a second item having a second molecular composition would generate a second diffraction signature, which is generally different than the first diffraction signature. Similarly, two items having a substantially same molecular composition would generate substantially similar diffraction signatures when exposed to radiation having a same energy. Accordingly, the diffraction signature can be used to label the item 102 (e.g., the item 102 is a piece of fruit, a piece of metal, an explosive, etc.) and/or to determine whether the item 102 is an item of interest (e.g., such as a potential threat item).

By way of example, in the illustrated environment, the diffraction system 100 comprises a diffraction signature comparison component 132 that is operably coupled to the diffraction signature component 130 and is configured to compare the diffraction signature of the item 102 to a set of diffraction signatures of known items. As an example, the diffraction signature comparison component 132 may be configured to compare the diffraction signature of the item 102 to a set of diffraction signatures of various organic explosives to determine whether the item 102 may be an organic explosive. If the diffraction signature substantially matches the diffraction signature of an organic explosive, the diffraction signature comparison component 132 may issue an alert to a terminal 134 configured to alert security personnel of a positive identification. Further, by comparing the diffraction signature of the item 102 to the diffraction signature of one or more known items (e.g., having known molecular compositions), the diffraction signature comparison component 132 may be configured to determine the molecular composition of the item 102 (e.g., if the diffraction signature of the item 102 matches a diffraction signature of a known item, the item 102 has a substantially same molecular composition as the known item).

Information regarding the comparison, such as whether a positive match occurred or did not occur, may be output from the diffraction signature comparison component 132 to the terminal 134, or workstation (e.g., a computer), configured to process the information and/or display the information on a monitor 136 to a user 138 (e.g., security personnel, medical personnel, etc.) in textual, graphical, or other human perceptible form, for example. The terminal 134 can also be configured to receive user input that can direct operations of the examination unit 106 (e.g., the positioning the radiation source 112 and/or detector array 114, movement of the object 104 by the support article 108, etc.).

In the example diffraction system 100, a controller 140 is operably coupled to the terminal 134. In some embodiments, the controller 140 is configured to receive user input from the terminal 134 and/or instructions from the terminal 134 and to generate commands for the examination unit 106 indicative of operations to be performed.

It may be appreciated that the example diffraction system 100 is merely intended to describe an example layout and/or example components and is not intended to be interpreted as limiting the scope of the disclosure, including the scope of the claims. By way of example, the data acquisition component 128 may be part of the examination unit 106 and/or the detector array 114. As another example, the diffraction signature comparison component 132 may be replaced with a diffraction signature analysis component configured to analyze one or more properties of the diffraction signature to determine a molecular composition of the item 102 without comparing the diffraction signature of the item 102 to the diffraction signatures of one or more known items. As still another example, the diffraction system 100 may comprise more than one radiation source 112 and/or more than one detector array 114.

Figure 2:
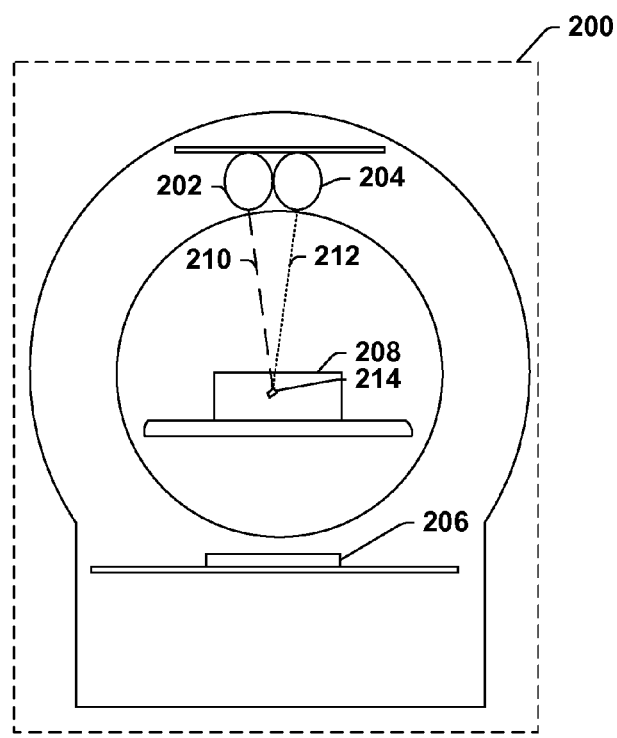
FIG. 2 illustrates an example examination unit of a diffraction system.

Referring to FIG. 2, an examination unit 200 (e.g., 106 in FIG. 1) of a diffraction system (e.g., 100 in FIG. 1) comprising two radiation sources 202, 204 (e.g., 112 in FIG. 1) and a single detector array 206 (e.g., 114 in FIG. 1) is provided. The two radiation sources 202, 204 are positioned substantially diametrically opposite the detector array 206 relative to an object 208 undergoing examination, and radiation beams 210, 212 emitted from respective radiation sources 202, 204 are directed toward an item 214 of interest within the object 208.

In such a configuration, radiation photons emitted from the radiation sources 202, 204 are detected by a same detector array 206 and data indicative of a radiation event is resolved to identify the source of the detected radiation photon. In some embodiments, the data is resolved temporally. For example, the radiation sources 202, 204 may be pulsated in a rotating fashion (e.g., where the first radiation source 202 is activated/opened while the second radiation source 204 is deactivated/closed and vice-versa). Data indicative of radiation photons detected while the first radiation source 202 is activated/opened are assumed to have been emitted by the first radiation source 202 and data indicative of radiation photons detected while the second radiation source 204 is activated/opened are assumed to have been emitted by the second radiation source 204.

In other embodiments, the data is resolved based upon the energy of the associated radiation photon when the radiation event occurred (e.g., when the radiation photon was detected by the detector array 206). By way of example, the first radiation source 202 may be configured to emit monoenergetic radiation beams 210 having a first energy level (e.g., 150 keV) and the second radiation source 204 may be configured to emit monoenergetic radiation beams 212 having a second energy level (e.g., 200 keV). Accordingly, coherent scatter yielded from the first radiation source 202 will have an energy of approximately 150 keV and coherent scatter yielded from the second radiation source 204 will have an energy of approximately 200 keV.

When a radiation photon impinges the detector array 206 (e.g., when a radiation event occurs), the detector array 206 may measure the energy of the incident radiation photon. When the data is resolved, data corresponding to a first set of radiation photons having an energy of approximately 150 keV may be resolved as being associated with the first radiation source 202 (e.g., the first set of radiation photons were generated by the first radiation source 202) and data corresponding to a second set of radiation photons having an energy of approximately 200 keV may be resolved as being associated with the second radiation source 204 (e.g., the second set of radiation photons were generated by the second radiation source 204). Data corresponding to detected radiation photons that do not measure about 150 keV or about 200 keV may correspond to incoherent scatter and may be discarded and/or ignored, for example (e.g., when determining a diffraction signature of the item 214).

In some embodiments, the use of two or more radiation sources (e.g., configured to emit radiation at different energy levels or at different energy spectrums) may be useful to determine the molecular composition of an item and/or to determine whether an item is an item of interest. By way of example, a potential threat item having a first molecular composition and a non-threat item having a second molecular composition may produce similar diffraction signatures at a first energy level, but may produce distinctly different diffraction signatures at a second energy level. For example, at 150 keV, differences between the diffraction signature of the potential threat item and the diffraction signature of the non-threat item may be indistinguishable. However, at 200 keV, differences between the diffraction signature of the potential threat item and the diffraction signature of the non-threat item may be distinguishable.

As another example, the availability of two or more radiation sources (e.g., configured to emit radiation at different energy levels or at different energy spectrums) may facilitate the selection of an energy level (e.g., or energy spectrum) based upon the content of a region comprising and/or spatially proximate the item 214 (e.g., surrounding the item 214 or in a beam path of the item 214). By way of example, when the content of a region comprising and/or spatially proximate the item 214 is known to comprise low density items (e.g., based upon a CT examination), a first radiation source 202, emitting radiation beams 210 at a low energy level, may be activated. When the content of the region is known to comprise higher density items, a second radiation source 204, emitting radiation beams 212 at a higher energy level, may be activated.

Figure 3:
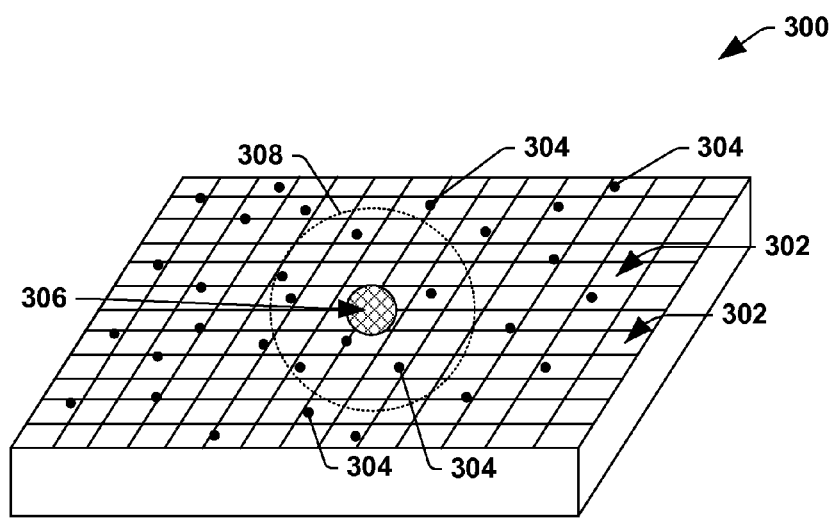
FIG. 3 illustrates an example detector array of a diffraction system.

Turning to FIG. 3, a perspective view of an example detector array 300 (e.g., 114 in FIGS. 1 and 206 in FIG. 2)

is illustrated. The detector array 300 may be an angular disbursement detector array or an energy disbursement detector array. Moreover, the detector array 300 may be a direct conversion detector array and/or an indirect conversion detector array.

The detector array 300 comprises a plurality of detector cells 302 (e.g., arranged into rows and columns in the example detector array 300) respectively configured to detect radiation photons 304 impingement upon the detector cell 302. In some embodiments, a physical mask 306 is placed over a portion of the detector array 300 intersecting a path of a radiation beam(s) emitted by the radiation source(s) to inhibit radiation photons that pass unimpeded through an item from being detected by the detector array 300 (e.g., so as to facilitate the detection of merely scattered radiation, including coherent scatter and/or incoherent scatter). In other embodiments, a dead zone may be created within the detector array 300 (e.g., where there are no detector cells 302) to inhibit such radiation photons from being detected and/or data yielded from detector cells 302, which detect such radiation photons may be disregarded by a diffraction signature component (e.g., 130 in FIG. 1), for example.

In some embodiments, a logical barrier 308 may be created for the detector array 300. The logical barrier 308 logically divides a region of the detector array 300 that is expected to detect a statistically significant portion of the incoherent scatter from a portion of the detector array 300 that is expected to detect a statistically insignificant portion of the incoherent scatter. The area within the logical barrier 308 (e.g., the area inside the circle) represents the portion of the detector array 300 that is expected to detect a statistically insignificant portion of the incoherent scatter (e.g., and a statistically significant portion of the coherent scatter), and the area outside of the logical barrier 308 (e.g., the area outside the circle) represents the portion of the detector array 300 that is expected to detect a statistically significant portion of the incoherent scatter (e.g., and a statistically insignificant portion of the coherent scatter). The size and/or shape of the logical barrier 308 may depend upon, among other things, the energy(ies) of radiation beams emitted by a radiation source(s). By way of example, at 160 keV, a statistically insignificant portion of the incoherent scatter and/or a statistically significant portion of the coherent scatter may be detected within a 5 degree cone relative to a linear path followed by the radiation beam(s) from the radiation source to the detector array. At 600 keV, a statistically insignificant portion of the incoherent scatter and/or a statistically significant portion of the coherent scatter may be detected within a 2 degree cone of the linear path. Accordingly, the diameter of the logical barrier 308 may be less if the radiation source(s) is emitting higher energy radiation (e.g., 600 keV radiation) as opposed to lower energy radiation (e.g., 160 keV radiation).

The logical barrier 308 may describe how data generated in response to detected radiation photons 304 is to be filtered. By way of example, data yielded from detector cells 302 within the logical barrier 308 may be utilized by a diffraction signature component (e.g., 130 in FIG. 1) when generating a diffraction signature of an item exposed to the radiation beam(s) while data yielded from detector cells 302 outside the logical barrier 308 may not be utilized when generating a diffraction signature (e.g., because detector cells 302 within the logical barrier 308 are likely to detect a statistically significant portion of coherent scatter and/or a statistically insignificant portion of incoherent scatter). Data yielded from detector cells 302 on the border of the logical barrier 308 may or may not be utilized by the diffraction signature component to generate the diffraction signature.

In other embodiments, no such logical barrier 308 is utilized because the data corresponding to coherent scatter may be discriminated from data corresponding to incoherent scatter based upon an energy of detected radiation photons 304, for example.

In some embodiments, the diffraction signature of an item is generated by plotting the radiation photons 304 detected by the detector array and/or a portion of the detected radiation photons 304 (e.g., such as merely the coherent scatter and/or merely those radiation photons 304 detected by detector cells within the logical barrier 308) to determine an angular disbursement of the radiation photons 304 (e.g., where the angular disbursement is indicative of the molecular structure of the item).

Figure 4:
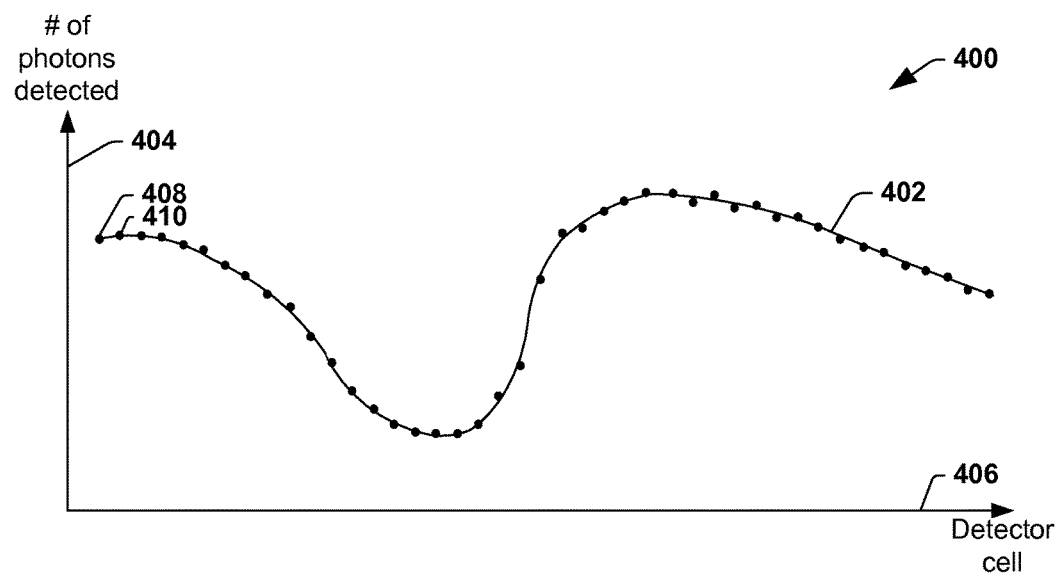
FIG. 4 illustrates an example diffraction signature yielded from data generated via a diffraction system.

FIG. 4 illustrates an example plot 400 describing an angular disbursement of radiation photons detected by a detector array. A diffraction signature 402 of an item targeted by a set of one or more radiation beams may be generated based upon the plot 400 using analytic, iterative, or other approaches. For example, in some embodiments, the diffraction signature 402 is generated by interpolating and/or extrapolating the data yielded from the detector array and/or a portion thereof.

A y-axis 404 of the plot 400 represents the number of photons detected during a measurement interval and the x-axis 406 represents detector cells. Accordingly, a first black dot 408 represents the number of photons (e.g., or the number of coherent photons) detected by a first detector cell during the measurement interval, a second black dot 410 represents the number of photons (e.g., or the number of coherent photons) detected by a second detector cell during the measurement interval, etc.

In some embodiments, a diffraction signature 402 of an item may be compared to known diffraction signatures of one or more known items to determine if the item is an item of interest. For example, in a security application, the diffraction signature 402 of the item may be compared to the known diffraction signatures of one or more organic explosives, non-organic explosives, and/or other potential threat items to determine if the item is a potential threat item.

In some embodiments, a diffraction signature 402 of an item may be utilized to determine a molecular composition of the item. For example, at a given energy level/spectrum, the angular disbursement of radiation photons may be different for different molecular compositions and thus peaks and/or valleys of the diffraction signature 402 may be different for different items. Accordingly, in some embodiments, the diffraction signature 402 may be analyzed to measure the placement and/or magnitude of peaks and/or valleys and/or to determine a molecular composition of the item (e.g., thus determining whether the molecular composition of the item is the similar to the molecular composition of an item of interest).

In some embodiments, the diffraction system is a secondary system utilized to examine an object and/or an item of potential interest within the object. By way of example, an object (e.g., suitcase, person, etc.) may initially undergo an examination via a first radiation imaging modality, such as a CT system and/or a line-scan system, and data generated therefrom may be analyzed to determine whether the object comprises a potential item of interest and/or whether there is an item that is indiscernible (e.g., an item that cannot be ruled out as an item of interest). For example, the data generated therefrom may be analyzed to determine whether the object comprises threat items. If an item is located that cannot be identified, with a specified degree of certainty, as a non-threat item based upon the data, the item may be subjected to additional examination by the diffraction system (e.g., to determine a molecular composition of the item).

Figure 5:
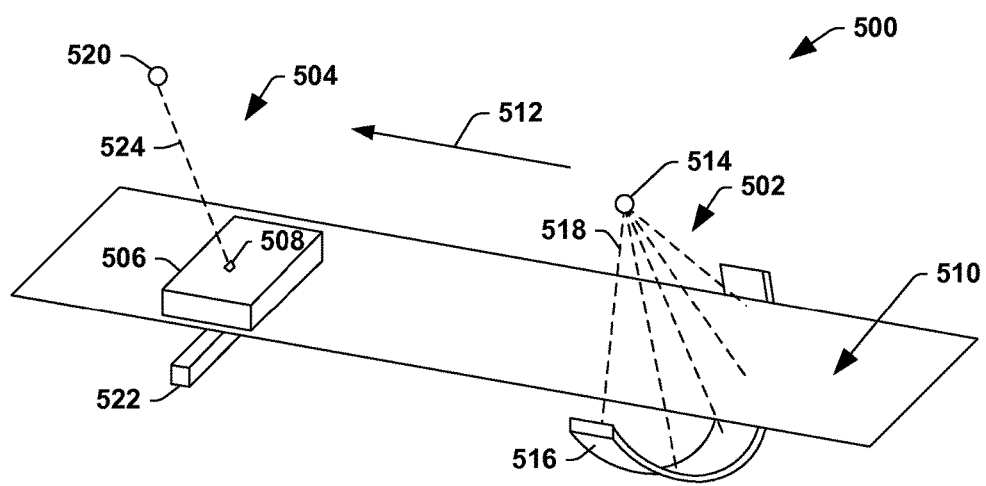
FIG. 5 illustrates an internal view of an example object identification system.

Turning to FIG. 5, an internal layout of an example object identification system 500 comprising a first examination modality 502 (e.g., an examination unit of a CT system, line-scan system, digital projection system, or other radiation imaging modality) and a second examination modality 504 (e.g., an examination unit of a diffraction system) is provided. The first examination modality 502 is configured to expose substantially all of an object 506 (e.g., 104 in FIG. 1) to radiation whereas the second examination modality 504 is typically configured to expose merely portions of the object 506, such as items within the object 506 that may be threat items, to radiation. Accordingly, the first examination modality 502 typically exposes a larger region of the object 506 to radiation than the second examination modality 502. Although, in some embodiments, the second examination modality 504 may substantially cover or blanket the object 506 with radiation through a series of successive (pencil-shape) radiation beams.

An object support 510 (e.g., 108 in FIG. 1) is configured to translate the object 506 through the object identification system 500. By way of example, the object support 510 may comprise a conveyor belt configured to receive the object 506 on an upstream portion of the object identification system 500 and to convey the object 506 to a downstream portion of the object identification system 500. In the illustrated embodiment, the object 506 is translated in a direction represented by the arrow 512.

The first examination modality 502 comprises a first radiation source 514 and a first detector array 516. In some embodiments, the first radiation source 514 and/or the first detector array 516 are configured to be rotated relative to the object 506. In some embodiments, the first radiation source 514 and the first detector array 516 are mounted to a rotating gantry configured to be rotated relative to the object 506 while a relative position between the first radiation source 514 and the first detector array 516 is maintained.

While the object 506 is within an examination region of the first examination modality 502, the first radiation source 514 is configured to emit cone, fan, wedge, or other shaped radiation 518 toward the object 506. The radiation 518 may be monoenergetic or non-monoenergetic (e.g., the radiation source 514 may emit radiation photons having a single energy level or a range of energy levels).

Radiation that traverses the object 506 and/or interacts with the object 506 is detected by the first detector array 516 and converted into data indicative of the object 506, which may be analyzed to determine the contents of the object 506 and/or to determine whether the object 506 comprises one or more items of interest (e.g., such as potential threat items). By way of example, the data may be analyzed to determine whether any portions of the object 506 have a shape, density, and/or Z-effective of the one or more items of interest.

While the object 506 is being examined by the first examination modality 502 and/or after the examination by the first examination modality 502 is complete, the object 506 may be translated to a second examination region where the object and/or items thereof may be further examined by a second examination modality 504 if such further examination is desired. By way of example, if the data generated by the first examination modality 502 indicates that the object 506 comprises an item of interest and/or if the data generated by the first examination modality 502 identifies an item 508 that is indiscernible from the data, the item 508 may be examined by the second examination modality 504 to verify that the item 508 is an item of interest and/or to rule-out the item 508 as an item of interest. In some embodiments, objects that do not contain an item of interest may traverse the second examination modality 504 without being examined and/or may be diverted so as to not traverse the second examination modality 504, for example.

The second examination modality 504 is typically configured to perform a more targeted examination of the object 506 and/or an item 508 (e.g., 102 in FIG. 1) thereof that may be of interest and comprises a second radiation source 520 (e.g., 112 in FIG. 1) and a second detector array 522 (e.g., 114 in FIG. 1). As described with respect to the examination unit 106 of FIG. 1 and/or the examination unit 200 of FIG. 2, the second radiation source 520 may comprise a radiographic isotope and/or may generate radiation when a bias is applied between an anode and a cathode of the second radiation source 520. Moreover, the second detector array 522 may be an angular disbursement detector array or an energy disbursement detector array, for example.

Typically, the second radiation source 520 is configured to emit (e.g., pencil-like) beams of radiation 524 toward an item 508 that is of particular interest based upon the data yielded from the first examination modality 502. Radiation emitted by the second radiation source 520 that traverses the object 506 may be detected by the second detector array 522 and converted into data, which may be analyzed to generate a diffraction signature of the item 508. The diffraction signature of the item 508 may be used to determine whether the item 508 is a threat item and/or to determine a molecular composition of the item 508. In this way, data yielded from the second examination modality 504 may be configured to confirm or verify whether the item 508 is an item of interest, for example.

Figure 6:
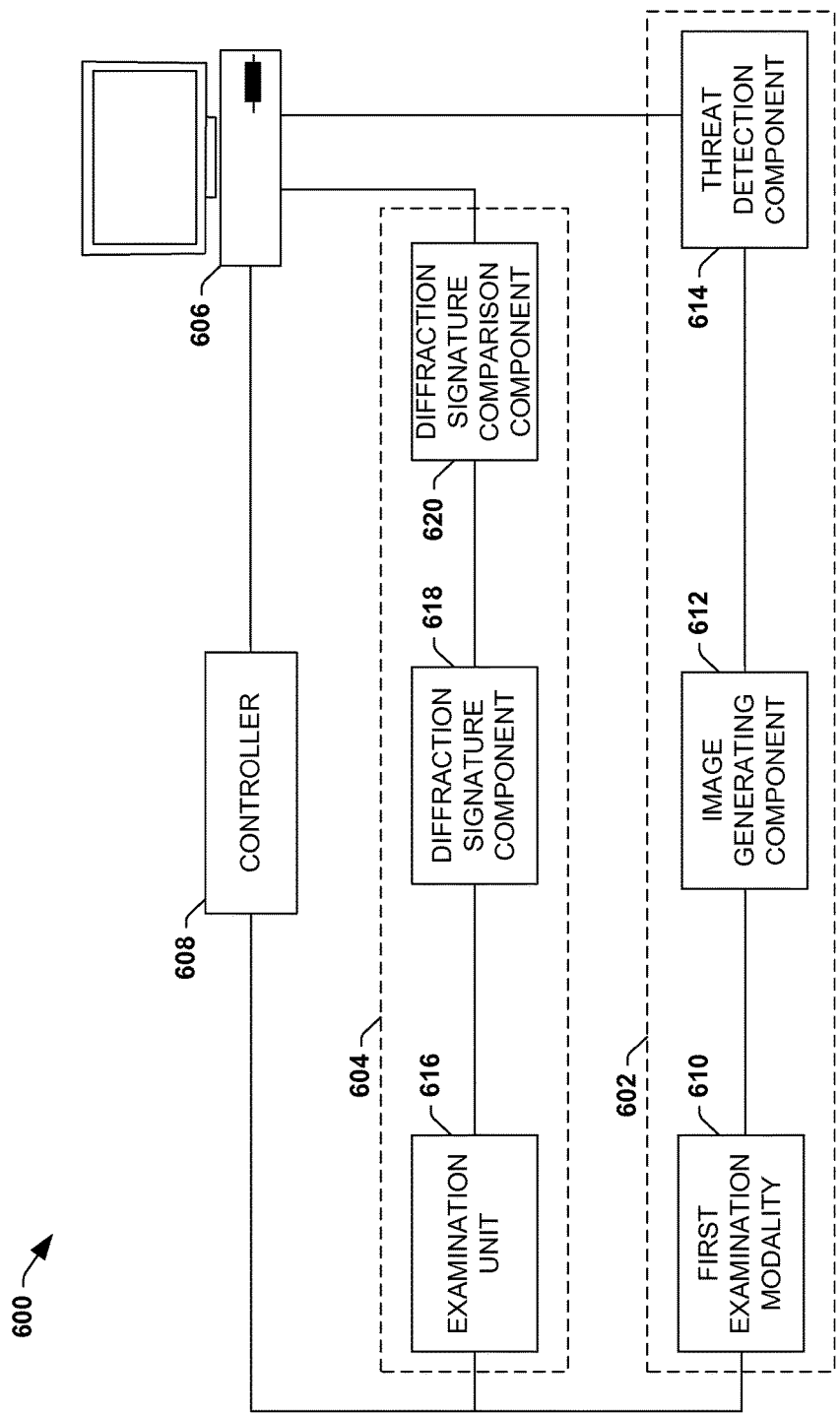
FIG. 6 is a schematic block diagram illustrating an example object identification system.

FIG. 6 provides a component block diagram of an example object identification system 600 comprising a first imaging modality 602, such as a CT system, line-scan system, or other radiation imaging modality, and a diffraction system 604 (e.g., 100 in FIG. 1). Data or other information output by the first imaging modality 602 and/or the diffraction system 604 is provided to a terminal 606 configured to process the information and/or generate instructions based upon the information and/or based upon user input. A controller 608 is operably coupled to the terminal 606 and is configured to provide commands to the first imaging modality 602 and/or the diffraction system 604 describing desired operations of the first imaging modality 602 and/or the diffraction system 604.

The first imaging modality 602 comprises a first examination modality 610 (e.g., 502 in FIG. 5), an image generating component 612, and a threat detection component 614. The first examination modality 610 is configured to examine an object via radiation and generate data based upon the radiation detected by a detector array of the first examination modality 610. Such data may include two-dimensional data and/or volumetric data. For example, in a line-scan system where a radiation source and detector array are typically fixed, causing an object to be viewed from a limited number of angles, the data output from the first examination modality 610 may be two-dimensional data. As another example, in a CT system where the radiation source and the detector array are typically rotated relative to the object, causing the object to be viewed from a plurality of angles, the data output from the first examination modality 610 may be volumetric data.

The image generating component 612 is configured to process the two-dimensional and/or volumetric data using analytical, iterative, or other image processing techniques (e.g., backprojection, tomosynthesis reconstruction, etc.) to generate one or more two-dimensional images and/or three-dimensional images of the object (e.g., converting the data from projection space to image space).

The image generating component 612 is operably coupled to the threat detection component 614 configured to analyze the two-dimensional image(s) and/or the three-dimensional image(s) to identify whether the object comprises one or more items to be further examined by the diffraction system. By way of example, the threat detection component 614 may analyze the image(s) to identify potential threat items concealed within the object. If the threat detection component 614 identifies a potential threat item and/or identifies an item that cannot be excluded as a potential threat item (e.g., with a specified degree of certainty) the threat detection component 614 may flag the item and/or may alert the terminal 606 of the item. It may be appreciated that while the example embodiment describes the threat detection component 614 as analyzing an image(s), in other embodiments, the threat detection component 614 may be configured to analyze projection space data instead of or in addition to the image(s).

When the terminal 606 receives an alert regarding an item, the terminal 606 may issue an instruction to the controller 608 to activate the diffraction system 604 to further examine the item. Responsive to such an instruction, the controller 608 may generate a command describing the spatial position of the item with respect to the object and/or describing a desired trajectory of a radiation beam(s) emitted by the diffraction system 604 (e.g., to cause the radiation beam(s) to interact with the item).

The diffraction system 604 is configured to examine targeted regions within the object, such as specific items, using (e.g., pencil-like) radiation beams. As described with respect to FIG. 1, the diffraction system 604 comprises, among other things, an examination unit 616, a diffraction signature component 618 (e.g., 130 in FIG. 1), and a diffraction signature comparison component 620 (e.g., 132 in FIG. 1). When the diffraction system 604 receives a command to examine an item(s) within the object, a radiation source of the examination unit 616 emits one or more beams of radiation at the item(s) to measure an angular disbursement of radiation photons that interact with the item(s). Based upon these measurements, the diffraction signature component 618 generates a diffraction signature of the item. The diffraction signature is indicative of an angular disbursement of at least some radiation photons detected by a detector array of the examination unit 616 and may be used by the diffraction signature comparison component 620 to determine whether the item is a threat item and/or to exclude the item as a threat item.

Figure 7:
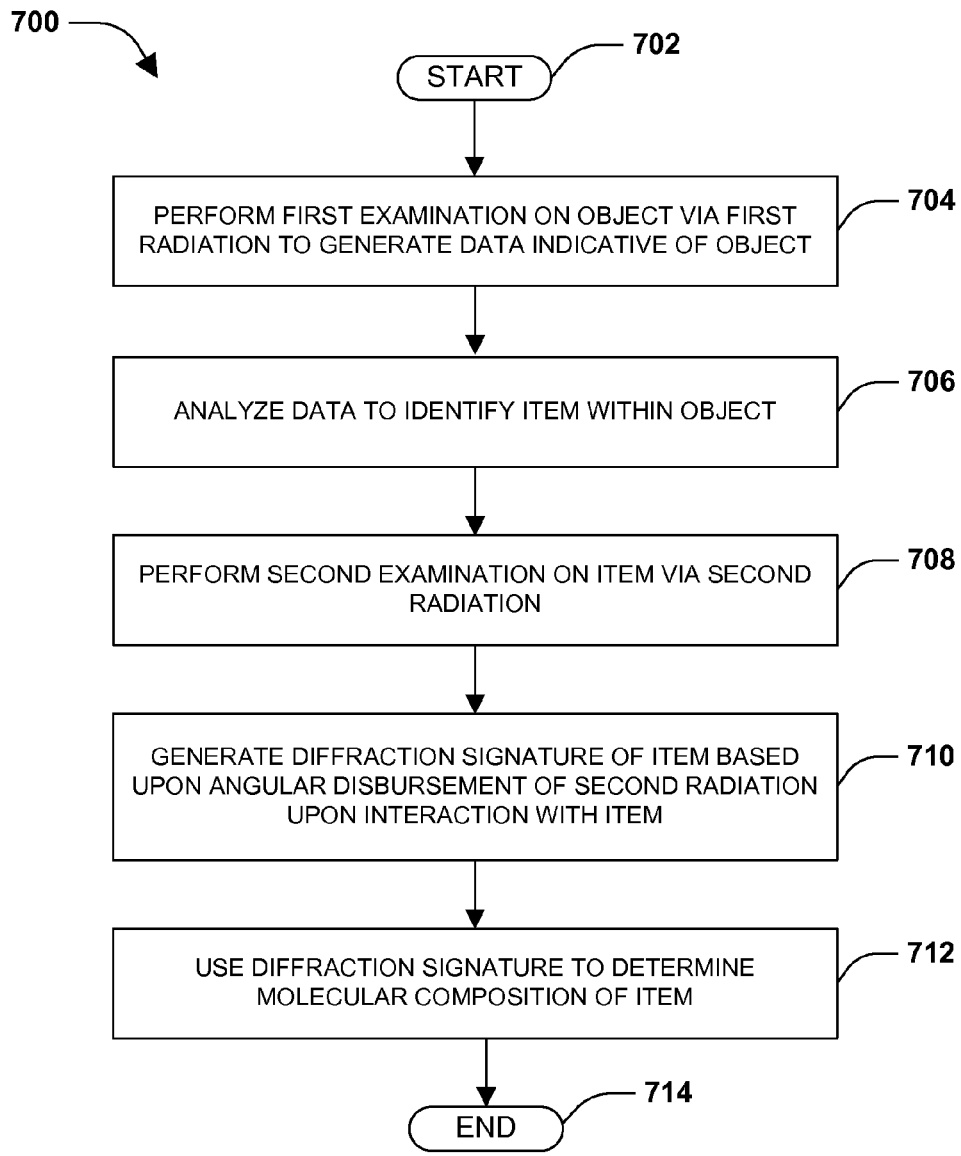
FIG. 7 is a flow diagram illustrating an example method for determining a molecular composition of an item within an object.

Referring to FIG. 7, a flow diagram of an example method 700 for performing an examination of an object comprising one or more items is provided. In some embodiments, such a method 700 may useful in security applications to identify potential threat objects and/or threat items therein.

The example method 700 starts at 702, and a first examination 704 is performed on the object via first radiation to generate data indicative of the object. The first examination may be a CT examination, line-scan examination, or other form of examination where the object is exposed to radiation and the attenuation of radiation is measured. In some embodiments, the radiation to which the object is exposed is monoenergetic. In other embodiments, the radiation to which the object is exposed is non-monoenergetic. In some embodiments, the radiation is emitted from a radiation source comprising a radiographic isotope. In other embodiments, the radiation is emitted from a radiation source comprising an anode and a cathode, which are biased to create a voltage potential between the anode and the cathode that causes radiation to be generated.

The data generated from the first examination may be two-dimensional data and/or volumetric data. Moreover, the data may be in projection space and/or in image space.

At 706 in the example method 700, the data generated from the first examination is analyzed to identify whether one or more items within the object satisfy specified criteria. By way of example, using a threat detection component, the data may be analyzed to determine whether the object comprises one or more potential threat items or other items of interest based upon the shape, density, Z-effective, or other characteristics of the items comprised within the object. As another example, the threat detection component may analyze the data to determine whether the object comprises an item that cannot conclusively be determined to be a non-threat item within a specified degree of confidence (e.g., and thus additional data would be useful to make such a determination).

At 708 in the example method 700, a second examination is performed when an item is identified that satisfies the specified criteria. In some embodiments, radiation generated from decay of a radiographic isotope is targeted at the item during the second examination and an angular disbursement of radiation photons that interact with the item is measured. In other embodiments, the radiation is generated based upon a voltage bias that is applied between an anode and a cathode of a radiation source emitting the radiation.

At 710 in the example method 700, a diffraction signature of the item is generated based upon an angular disbursement of the second radiation. That is, stated differently, a diffraction signature describing how radiation photons disburse upon interaction with the item is generated.

In some embodiments, the diffraction signature is indicative of the angular disbursement of merely a subset of the second radiation detected by a detector array. By way of example, the diffraction signature may be indicative of the angular disbursement of merely coherent scatter and/or may be indicative of the angular disbursement of radiation photons that were detected within merely a specified region of the detector array. Accordingly, in some embodiments, data yielded from the detector array is filtered prior to generating the diffraction signature. For example, data indicative of incoherent scatter of the second radiation may be filtered from data indicative of coherent scatter of the second radiation based upon the region of the detector array represented by the data and/or an energy of radiation photons associated with the data.

At 712 in the example method 700, the diffraction signature is used to determine a molecular composition of the item and/or to label the item (e.g., as a threat item, non-threat item, etc.). In some embodiments, the molecular composition of the item is determined by comparing the diffraction signature to a set of diffraction signatures of items having known molecular compositions to determine the molecular composition of the item and/or to determine whether the item is a member of a class of items of interest. By way of example, the diffraction signature of the item may be compared to the diffraction signature of one or more threat items to determine whether the item is a threat item (e.g., and has the molecular composition of a threat item) or is not a threat item (e.g., and does not have such a molecular composition).

At 714, the method 700 ends.

Figure 8:
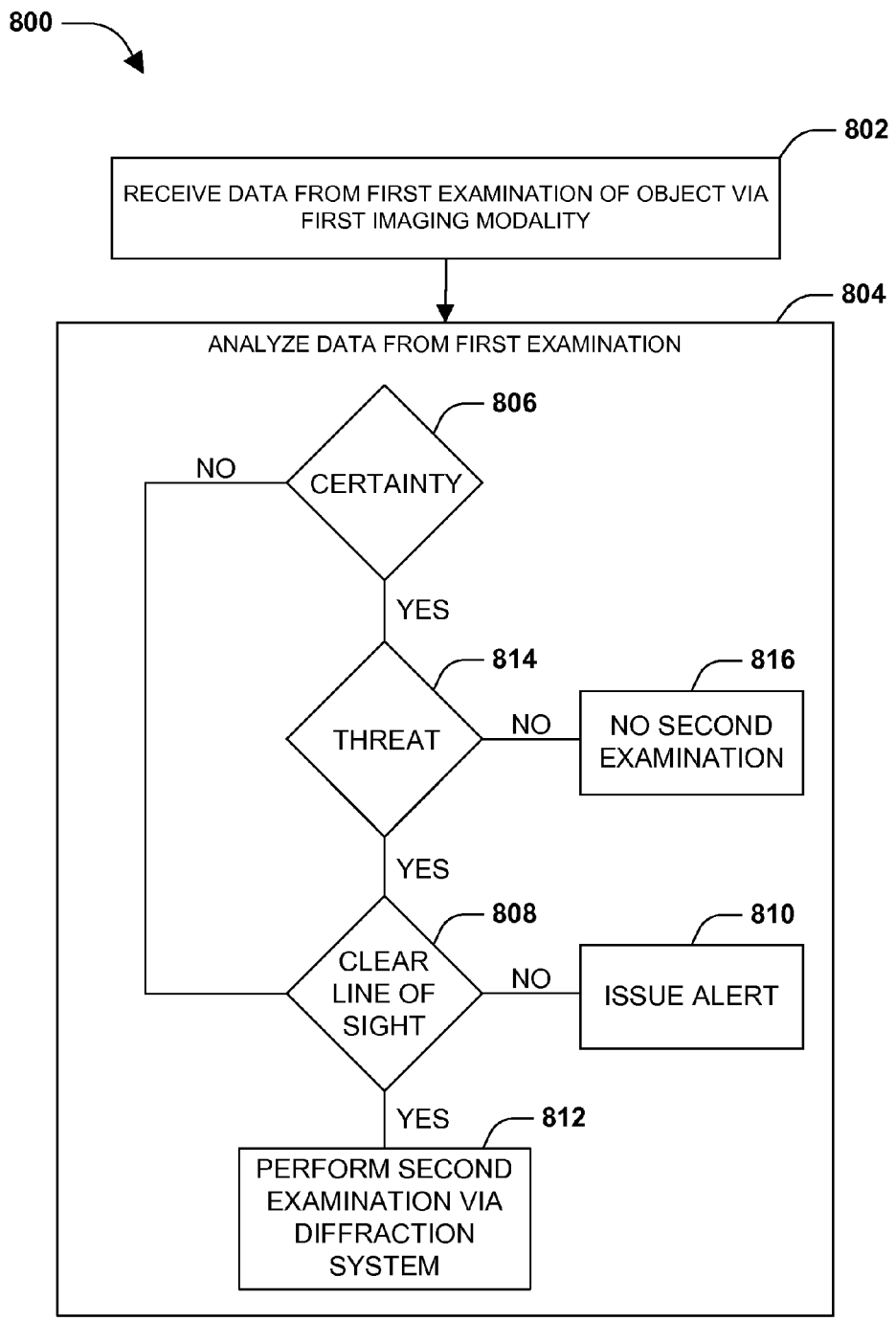
FIG. 8 is an example decision tree for determining whether to perform a second examination via a diffraction system.

FIG. 8 illustrates an example decision tree 800, which may be used (e.g., by a terminal) to assess the desirability of performing an examination on an item via a diffraction system. At 802 in the decision tree 800, data is received from a first examination of the object performed via a first radiation imaging modality, such as a CT system or a line-scan system. At 804 in the decision tree, the data is analyzed to determine whether to perform a second examination on the item via a diffraction system.

The analysis includes determining whether the object comprises one or more items that cannot be identified, with a specified degree of certainty, as non-threat items at 806. For example, an item may have a density, Z-effective, and/or shape characteristic that is similar to both a known non-threat item and a known threat item and/or such characteristics may not be discernible from the available data yielded from the first examination.

If the object comprises an item that cannot be identified with the specified degree of certainty, the terminal, for example, may evaluate at 808 data, from the first examination, corresponding to a region of the object spatially proximate the item to determine whether to perform the second examination. For example, the terminal may consider whether there is a clear line-of-sight for a radiation beam to traverse to interact with the item. If a metal plate or other high density item, for example, is in the path where a radiation beam would be targeted during the second examination, the metal plate or other high density item is likely to interfere with the second examination of the item (e.g., thus rendering the second examination futile). If the terminal determines that there is no clear line-of-sight, an alert may be issued to an operator, for example, at 810 notifying the operator that other screening techniques (e.g., such as a hand search) is desired. If the terminal determines that there is a clear line-of-sight, the terminal may request at 812 that a second examination be performed on the item via the diffraction system.

Returning to the decision at 806, if the object does not comprise one or more items that cannot be identified, with a specified degree of certainty, as non-threat items, the terminal may consider whether the object comprises a threat item at 814. If the terminal determines that the object does not comprise one or more threat items, the terminal may elect at 816 to forego a second examination on object via diffraction system. If the terminal determines that the object does comprise a threat item, the terminal, for example, may evaluate, at 808, data corresponding to a region of the object spatially proximate the threat item to determine whether to perform the second examination. For example, the terminal may consider whether there is a clear line-of-sight for a radiation beam to traverse to interact with the threat item. If the terminal determines that there is no clear line-of-sight, an alert may be issued to an operator, for example, at 810 notifying the operator that other screening techniques (e.g., such as a hand search) is desired. If the terminal determines that there is a clear line-of-sight, the terminal may request at 812 that a second examination be performed on the threat item via the diffraction system.

Figure 9:
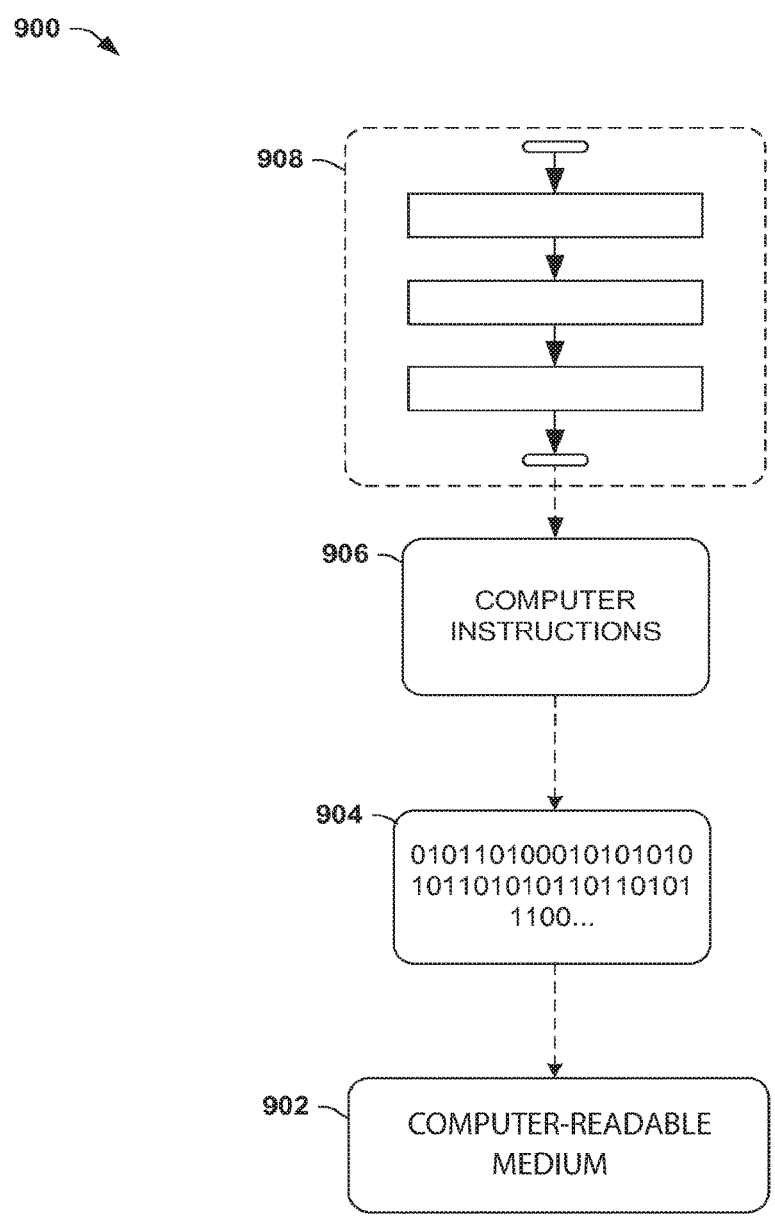
FIG. 9 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 9, wherein the implementation 900 comprises a computer-readable medium 902 (e.g., a flash drive, CD-R, DVD-R, application-specific integrated circuit (ASIC), field-programmable gate array (FPGA), a platter of a hard disk drive, etc.), on which is encoded computer-readable data 904. This computer-readable data 904 in turn comprises a set of processor-executable instructions 906 configured to operate according to one or more of the principles set forth herein. In one such embodiment 900, the processor-executable instructions 906 may be configured to perform a method 908 when executed via a processing unit, such as at least some of the example method 700 of FIG. 7 and/or at least some of 800 of FIG. 8, for example. In another such embodiment, the processor-executable instructions 906 may be configured to implement a system, such as at least some of the exemplary diffraction system 100 of FIG. 1 and/or example object identification system 600 of FIG. 6. Many such computer-readable media may be devised by those of ordinary skill in the art that are configured to operate in accordance with one or more of the techniques presented herein.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Moreover, "exemplary" is used herein to mean serving as an example, instance, illustration, etc., and not necessarily as advantageous. As used in this application, "or" is intended to mean an inclusive "or" rather than an exclusive "or." In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used in either the detailed description or the claims, such terms are intended to be inclusive in a manner similar to the term "comprising."

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

As used in this application, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. A system for generating a diffraction signature of an item within an object, comprising:
    a threat detection component configured to analyze data indicative of the object to identify the item, wherein the data comprises two-dimensional data generated from a line-scan examination of the object;
    a radiation source comprising a radiographic isotope configured to expose the item to radiation;
    a first positioning apparatus to which the radiation source is coupled, the first positioning apparatus configured to move the radiation source relative to the object based upon a position of the item within the object;
    a detector array configured to detect radiation that interacts with the item; and
    a diffraction signature component configured to generate the diffraction signature of the item based upon an angular disbursement of the radiation that interacts with the item.

2. The system of claim 1, wherein the diffraction signature comparison component is configured to compare the diffraction signature to a set of diffraction signatures of items of interest to determine if the item is an item of interest.

3. The system of claim 1, further comprising:
    a second positioning apparatus to which the detector array is coupled, the second positioning apparatus configured to move the detector array relative to the object based upon the position of the item within the object.

4. The system of claim 1, further comprising a line-scan apparatus configured to generate the two-dimensional data, wherein the line-scan apparatus comprises:
    a second radiation source; and
    a second detector array configured to detect radiation emitted by the second radiation source.

5. The system of claim 1, wherein the radiation source is configured to expose the item to monoenergetic radiation.

6. The system of claim 1, wherein the detector array comprises an energy disbursement detector array configured to measure an energy of the radiation that interacts with the item to distinguish incoherent scatter from coherent scatter.

7. The system of claim 1, wherein the radiographic isotope comprises at least one material selected from the group consisting of cesium-137 and cobalt-57.

8. A method for determining a molecular composition of an item within an object, comprising:
    performing a first examination on an object via first radiation to generate data indicative of the object by moving a source of the first radiation relative to the object based upon a position the item within the object;
    analyzing the data to identify the item within the object;
    performing a second examination on the item via second radiation generated from decay of a radiographic isotope, comprising:
        filtering data indicative of incoherent scatter of the second radiation from data indicative of coherent scatter of the second radiation;
    generating a diffraction signature of the item based upon an angular disbursement of the second radiation upon interaction with the item; and
    using the diffraction signature to determine a molecular composition of the item.

9. The method of claim 8, wherein:
    the first radiation comprises radiation photons having a range of energy levels, and
    the second radiation is monoenergetic.

10. The method of claim 8, wherein the performing a first examination on an object via first radiation to generate data indicative of the object comprises examining the object from a plurality of view-angles.

11. The method of claim 8, wherein the filtering data indicative of incoherent scatter of the second radiation from data indicative of coherent scatter of the second radiation comprises filtering the data indicative of incoherent scatter from the data indicative of coherent scatter based upon an energy level of detected radiation from the second examination.

12. The method of claim 8, wherein the using the diffraction signature to determine a molecular composition of the item comprises comparing the diffraction signature to a set of diffraction signatures of items having known molecular compositions to determine the molecular composition of the item.

13. The method of claim 8, wherein the analyzing the data to identify the item within the object comprises evaluating a region of the object spatially proximate the item to determine whether to perform the second examination.

14. The method of claim 8, wherein the generating a diffraction signature of the item based upon an angular disbursement of the second radiation upon interaction with the item comprises generating the diffraction signature of the item based upon the angular disbursement of the coherent scatter.

15. A system for generating a diffraction signature of an item within an object, comprising:
    a radiation source comprising a radiographic isotope configured to expose the item to radiation;
    a first positioning apparatus to which the radiation source is coupled, the first positioning apparatus configured to move the radiation source relative to the object based upon a position of the item within the object;

a detector array configured to detect radiation that interacts with the item, wherein the detector array comprises an energy disbursement detector array configured to measure an energy of the radiation that interacts with the item to distinguish incoherent scatter from coherent scatter; and a diffraction signature component configured to generate the diffraction signature of the item based upon an angular disbursement of the radiation that interacts with the item.

16. The system of claim 15, further comprising a threat detection component configured to analyze data indicative of the object to identify the item.

17. The system of claim 15, further comprising a diffraction signature comparison component configured to compare the diffraction signature to a set of diffraction signatures of items of interest to determine if the item is an item of interest.

18. The system of claim 15, further comprising a second positioning apparatus to which the detector array is coupled, the second positioning apparatus configured to move the detector array relative to the object based upon the position of the item within the object.

\* \* \* \* \*

UNITED STATES PATENT AND TRADEMARK OFFICE
CERTIFICATE OF CORRECTION

PATENT NO. : 10,261,212 B2
APPLICATION NO. : 14/907325
DATED : April 16, 2019
INVENTOR(S) : David Schafer and John P. O'Connor Page 1 of 1

It is certified that error appears in the above-identified patent and that said Letters Patent is hereby corrected as shown below:

In the Specification
Column 10, Line 67, change "in FIGS. 1 and 206 in FIG. 2)" to --in FIG. 1 and 206 in FIG. 2)--

Signed and Sealed this
Eighteenth Day of June, 2019

Andrei Iancu
*Director of the United States Patent and Trademark Office*